United States Patent [19]

Dallas

[11] Patent Number: 5,137,721
[45] Date of Patent: Aug. 11, 1992

[54] EMPLOYING STRAINS OF E. COLI EXPRESSING NON-INDIGENOUS ADHESINS AND TOXOIDS OF E. COLI

[75] Inventor: Walter S. Dallas, San Pablo, Calif.

[73] Assignee: Cetus Corporation, Emeryville, Calif.

[21] Appl. No.: 307,223

[22] Filed: Feb. 6, 1989

Related U.S. Application Data

[63] Continuation of Ser. No. 201,318, May 26, 1988, abandoned, and a continuation of Ser. No. 293,585, Jan. 4, 1989, abandoned, which is a continuation of Ser. No. 658,452, Oct. 5, 1984, abandoned, which is a continuation of Ser. No. 487,995, Apr. 27, 1983, abandoned, which is a continuation of Ser. No. 241,594, Mar. 9, 1981, abandoned.

[51] Int. Cl.$^5$ .................. A61K 39/108; C12N 1/21; C12N 15/00
[52] U.S. Cl. .................. 424/93 A; 424/92; 435/252.33; 435/172.3; 435/69.3

[56] References Cited

U.S. PATENT DOCUMENTS

| 4,237,224 | 2/1980 | Cohen et al. | 435/68 |
| 4,337,314 | 6/1982 | Oeschger et al. | 435/253 |
| 4,338,298 | 7/1982 | Myers | 424/92 |
| 4,394,443 | 7/1983 | Weissman | 435/6 |

FOREIGN PATENT DOCUMENTS

| 0001930 | 6/1979 | European Pat. Off. . |
| 0060129 | 9/1982 | European Pat. Off. . |
| 060129 | 9/1982 | European Pat. Off. . |
| 168322 | 1/1986 | European Pat. Off. . |
| 172107 | 2/1986 | European Pat. Off. . |
| 7526861 | 3/1976 | France . |
| 8002504 | 11/1980 | PCT Int'l Appl. ........ 424/92 |
| 1462524 | 5/1977 | United Kingdom . |
| 1472624 | 5/1977 | United Kingdom . |

OTHER PUBLICATIONS

Shipley et al. (1979) *Microbiology* (ASM) pp. 176-180.
Dallas et al. (1979) *Journal of Bacteriology* vol. 139 pp. 850-858.
So et al. (1978) *Infection and Immunity* vol. 21 pp. 405-411.
Dallas et al. (1980) *Nature* vol. 288 pp. 495-501.
Broda *Plasmids* 1979 Freedman and Co. Ltd. pp. 120-123 San Francisco.
Silva, et al., Isolation and characterization of enterotoxin-deficient mutents of *E. coli Proc. Natl. Acad. Sci. USA* vol. 75, 1978 p. 1384-1388.
P. L. Shipley et al., Identification and Cloning of the Genetic Determinant that Encodes for the K88ac Adherence Antigen J. Bacteriology 145, 920-925 (1981).
J. D. A. van Embden et al., Cloning and Expression of a Deoxyribonucleic Acid Fragment that Encodes for the Adhesive Antigen K99, Infect. Immun. 29, 1125-1133 (1980).
F. R. Mooi et al., Cloning, Mapping and Expression of the Genetic Determinant that Encodes for the K88ab Antigen, Nucleic Acids Research 6, 849-865 (1979).
J. Rutter et al. Antibacterial Activity in Colostrum and Milk Associated with Protection of Piglets Against Enteric Disease Caused by K88-positive *Escherichia coli*, Infect. Immun. 13, 667-676 (1976).
J. M. Rutter and G. W. Jones, Protection against Enteric Disease caused by *Escherichia coli*—a Model for Vaccination with a Virulence Determinant, Nature 242, 531-532 (1973).
Moon, H. W. *Adv. Vet. Sci. and Compt. Med.* 18:179-211 (1974).
Kohler, E. M., *Am. J. Vet. Res.* 29:2263-2274, (1968).
Gyles, C. L. & Barnum, D. A., *J. Inf. Dis.* 120:419-426 (1968).
*Science*, "Vaccinating with Bacterial Pilip" 209:1103-1106, Sep. 1980.
Dobrescu and Huygelen, *Zpl. Det. Med. B.*, 23:79-88 (1976).
Jones and Rutter, *Am. J. of Clinical Nutrition*, 27:1441-1449, (Dec. 1974).
Morgan et al., *Infect Immun.* 22:771-777 (Dec. 1978).
Nagy, *Infect. Immun.*, 27:21-24 (Jan. 1980).
Guinee, Veldkamp, Jansen, *Infect. Immun.* 15:676-678 (1977).
Dallas and Falkow, *Infect. Immun.*, 21:405-411 (1978).
Clements and Findelstein, *Infect. Immun.*, 22:709-713 (1978).
Gyles, *Infect. Immun.*, 9:564-569 (1974).
Gyles et al., *J. Infect Dis.*, 130:40-49 (1974).
Jones, G. W. and Rutter, J. M. *Infect. Immun.* 6:918-927 (1972).
Marx, J. L., Science 209:1103-1106 (Sep. 1980).
Moselay et al., *J. Bacteriol*, pp. 444-446 (1980).
Bolivar et al., Methods in Enzymology, 68:245-267 (1979).
Dallas, et al., *Microbiology*, pp. 233-236 (1979).
Dallas, et al., *Plasmids of Medical, Environmental and Commercial Importance*, 1:113-122 (1979).

*Primary Examiner*—Douglas W. Robinson
*Assistant Examiner*—Marian C. Knode
*Attorney, Agent, or Firm*—Lewis S. Gruber; Philip L. McGarrigle

[57] ABSTRACT

A vaccine is described for prevention of gastro-enteric disease caused in a mammalian species by a pathogenic microorganism. The vaccine comprises a non-pathogenic microorganism strain containing stable replicative plasmids, each having one or more genes non-indigenous to the plasmid. The non-indigenous genes are either genes for an adhesin necessary for adherence of the pathogenic microorganism in the mammalian species or are genes for toxoids of toxins causative of the disease. Both types of genes may also be included in the same plasmid.

17 Claims, No Drawings

EMPLOYING STRAINS OF *E. COLI* EXPRESSING NON-INDIGENOUS ADHESINS AND TOXOIDS OF *E. COLI*

This application is a continuation of application Ser. No. 201,318, filed May 26, 1988 and a continuation of Ser. No. 293,585, filed Jan. 4, 1989, which is a continuation of Ser. No. 658,452, filed Oct. 5, 1984, which is a continuation of Ser. No. 487,995, filed Apr. 27, 1983, which is a continuation of Ser. No. 241,594, filed Mar. 9, 1981, all abandoned.

This invention relates generally to the field of immunology and, more particularly, to an improved vaccine for prevention of gastro-enteric disease. The invention also relates to an improved method of vaccinating a mammalian species using such a vaccine and to an improved method for producing such a vaccine.

Many gastro-enteric diseases in humans and animals, such as those caused by *Escherichia coli* and similar bacteria, are generally the result of toxin production which operates to disrupt the fluid balance in the gastro-intestinal tract. The result is excessive production of fluids and electrolytes from the epithelial cells in the gastro-intestinal tract. (Moon, H. W., *Adv. Vet. Sci. and Compt. Med.*, 18:179-211 (1974).) By way of example, certain strains of *E. coli* cause a cholera-like disease in humans and young farm animals which may result from the action of either of two toxins that have been isolated and identified as ST, which is heat stable, and LT, which is heat labile. Kohler, E. M., *Am. J. Vet. Res.* 29:2263-2274, (1968); Gyles, C. L. & Barnum, D. A., *J. Inf. Dis.* 120:419-426 (1968).

Recent studies have shown that in order for pathogens to successfully colonize parts of the body, it is necessary for the pathogen to have the ability to adhere to the cell surfaces so that it can multiply. After colonization, the pathogens produce agents, such as toxins, which cause the undesirable symptoms. *Science* 209:1103-1106, September 1980. The adhesins necessary for this adherence are typically structures called pili, which are thread-like projections on bacterial cell surfaces and are typically necessary if the pathogen is to cause disease.

It has been established that immunity to pathogens can be conferred by immunizing against the toxins which they produce; Dobrescu, L., and Huygelen, C., *Zpl. Det. Med. B*, 23:79-88 (1976), and by immunizing against the adhesin factor, Jones, G. W., and Rutter, J. M., *Am. J. of Clinical Nutrition*, 27:1441-1449, (December 1974); Nagy, B., *Infect. Immun.*, 27:21-24, (January 1980). Vaccines conferring such immunities have been prepared with killed pathogens which themselves contained genes for producing the offending substances. In addition, vaccines have been prepared using the pure adhesin itself.

Preparation of vaccines in the ways referred to above leads to a number of serious problems. If the pathogen itself is used, the pathogen must be attenuated or killed in order to avoid causing the infection which the vaccination is designed to prevent. Of course, this requires a high degree of quality control in the manufacture of the vaccine to ensure proper attenuation or killing of the pathogen. Moreover, manufacturing vaccines of this type in this way necessitates providing growth conditions for large amounts of pathogens which, in the case of human diseases, are potential infectants of the human beings associated with the manufacturing process. Additionally, great care must be taken to insure that the live pathogens do not escape to the surrounding environment.

A further problem with many pathogens is that created by so-called capsular antigens. These polysaccharide layers cause alteration in the surface antigens exposed to potential antibody reaction. Consequently, a set of antibodies stimulated by one type of vaccine may be ineffective against the same pathogen with altered surface characteristics resulting from capsular antigens. This, as well as the other problems mentioned above, add cost and complexity to the manufacture of vaccines in this way.

Vaccines have, as mentioned above, been developed using purified pili which are capable of causing an antibody response in a vaccinated host. Morgan, R. L., Isaacson, R. E., Moon, H. W. and To, C. C., *Infect. Immun.* 22:771-777 (December 1978). However, purification of the desired substance can be an exceedingly difficult and expensive procedure, greatly increasing the cost of such vaccines.

Accordingly, it is an object of the present invention to provide an improved type of vaccine.

Another object of the invention is to provide an improved vaccine comprising a non-pathogenic microorganism.

Another object of the invention is to provide an improved vaccine employing toxoids or adhesins as the antigenic determinants but which does not require purification and isolation of such substances.

Other objects of the invention will become apparent to those skilled in the art from the following description.

Very generally, the vaccine of the invention comprises a non-pathogenic microorganism strain containing stable replicative plasmids, each having a gene or genes non-indigenous to the plasmid. The genes are either genes for an adhesin necessary for adherence of the pathogenic microorganism in the mammalian species, or genes for toxoids of a toxin causative of the disease. Combinations of the two types of genes are also possible.

The invention takes advantage of the newly emerging technology of recombinant DNA. By using such techniques, microorganisms can be genetically engineered which are harmless but which make a protein product which stimulates production of desired antibodies. The genes which are inserted into the host microorganism are inserted by means of plasmid cloning vectors. The genes are either genes for an adhesin necessary for adherence of the pathogenic microorganism being vaccinated against, or genes for toxoids of a toxin causative of the disease. In some cases, both types of genes will be used. In any case, the non-pathogenic host in which the genes have been inserted manufactures the proteins encoded by those genes, thus enabling the vaccinated subject to produce antibodies in response to such proteins. These antibodies will then confer immunity against all other microorganism species which manufacture those proteins including, of course, pathogenic species.

In the case of adhesins, there are four known K88 types, ab, ac, ad and ad(e). K88(ac) and K99 have been cloned successfully. These adhesins are factors in neonatal diarrhea in piglets, calves and lambs. They have also been proven to be the important immunogen antigenically determinant in provoking the protective response. Jones, G. W. and Rutter, J. M., *Am. J. of Clin. Nutr.*, 27:1441-1449 (December 1974); Guinee, P. A.

M., Veldkamp, J., and Jansen, W. H., *Infect. Immun.* 15:676–678 (1977). The gene for the heat labile toxin LT has been cloned, So, M., Dallas, W. S., and Falkow, S., *Infect. Immun.*, 21:405–411 (1978). Also, the gene for one subunit of LT, LT-B, a non-deleterious part of the toxin, has been cloned. LT-B has been shown to be determinant in stimulating the antibody response to the toxin LT.

LT has been demonstrated to be very similar to the toxin responsible for human cholera, Clements, J. D., and Finkelstein, R. A., *Infect. Immun.* 22:709–713 (1978); Gyles, C., *Infect. Immun.* 9:564–569 (1974); Dallas, W. S., and Falkow, S., *Nature* 288:499–501. Thus, LT-B can be successfully employed in live non-pathogenic microorganisms as a vaccine for this disease as well as for many of the *E. coli* produced diseases.

The following examples are given as representative of the invention. However, the claims are intended to encompass all forms of the invention and are not intended to be limited by such examples.

EXAMPLE I

Diarrheal disease in piglets is often caused by *E. coli* that produce two types of enterotoxins, LT (heat labile toxin) and ST (heat stable toxin). Both of these toxins are plasmid mediated., Gyles, C., So, M., and Falkow, S., *J. Infect. Dis.* 130:40–49 (1974). *E. coli* strains producing such toxins frequently have a surface antigen composed of identical subunits that form filamentous surface appendages or pili and which give the pathogenic strain its adhesive properties for the epithelial cells of the upper intestine. Jones, G. W. and Rutter, J. M. *Infect. Immun.* 6:918–927 (1972). A form of this antigen, K88, exists in at least four serologically distinguishable varieties known as K88ab, K88ac, K88ad and K88ad(e).

The K88 gene (K88ac) was first cloned at the University of Washington in Seattle. Shipley, P. L., Dallas, W. S., Dougan, G, and Falkow, S. *Microbiology*, 1979 (American Society for Microbiology, p. 176–180). Although the specific technique has not been published, it is essentially a standard cloning technique.

To accomplish this the plasmid pPS100 which is 90 Kb in size, is cleaved with the restriction enzyme, HindIII. A 7.8 Kb DNA fragment, that includes the K88 gene, is inserted into the HindIII site in the plasmid pBR322, producing a plasmid 12.1 Kb in size, designated pPS002. This plasmid retains a functional gene for resistance to ampicillin ($Amp^R$) which enables the direct selection for transformants of *E. coli* K-12 harboring the plasmid. These transformants are then screened for tetracycline sensitivity ($Tet^S$) due to the insertion of a DNA fragment in the HindIII site of pBR322 which inactivates the gene controlling resistance to tetracycline. $Tet^S$ transformants are then tested for K88 production using K88 antibody. A small (4.8 Kb) fragment cut by the restriction enzyme EcoRI may then be removed to make the K88 plasmid less of a handicap to the host cell.

In actually reducing this portion of the invention to practice, several positive clones resulted from the screening process. All these clones have the same HindIII fragment, all were identical in observable phenomena, and all synthesized approximately four times as much K88 antigen as a wild type pathogenic strain as determined by radioimmunoassay. Although the cloning vector existed in the host at 10-20 copies per cell, the production of K88 was lower than 10-20 times that of the wild type, probably due to as yet unappreciated physiological controls in the host. These strains may then be used live, or may be attenuated or killed by known vaccination preparation techniques, in a vaccine preparation. Use may be in accordance with any suitable known vaccination technique, but is preferably administered to sows as a challenge at six weeks, and again at four weeks, prior to farrowing using a single subcutaneous injection each time.

EXAMPLE II

K99 is a similar adhesin or pili which is responsible for a certain amount of enteric disease in pigs, and for a relatively larger amount of enteric disease in lambs and calves. In preparing a K99 containing vaccine, protocols are used essentially identical to those followed in Example I in connection with K88. The plasmid used was designated pBR313 ($Tet^R Amp^R$) and selection was for $Amp^R$, $Tet^S$, and agglutination with K99 antibody. The result was a plasmid pWD010 (15.45 Kb).

Once again, the vaccine may be utilized in the live state, or may be attenuated or killed in accordance with known procedures. Vaccination results may be successfully achieved by challenging with the vaccine subcutaneous injections of pregnant sows, ewes, or cows, six weeks, and again at four weeks, prior to farrowing using a single subcutaneous injection each time.

EXAMPLE III

It is, of course, possible to create a vaccine by mixing organisms producing K88 with organisms producing K99. However, such a technique involves separate growth of two different types of the organism. For manufacturing purposes, it may be desirable to produce the two pili factors or adhesins in a single organism. There are two ways of doing this. This example deals with a situation in which a single organism contains two different plasmids, one of which contains the K88 gene and the other of which contains the K99 gene. The immediately following example, Example IV, illustrates the technique utilizing a single plasmid containing both the K88 and K99 gene.

The plasmids constructed in Example I containing the K88 genes were designated pPS002. The plasmid of Example II, pWD010, containing the K99 gene was derived from the plasmid pBR313. Since the plasmid pPS002 containing the K88 genes was derived from the plasmid pBR322, both plasmids pPS002 and pWD010 belong to the same incompatibility group. Only plasmids which are members of different incompatibility groups can stably exist together. Accordingly, the K99 gene of pWD010 was cloned as a BamH-I fragment into a tetracycline resistance ($Tet^R$) gene of a plasmid designated pACYC184, producing a plasmid designated pCTS3002 (10.65 Kb). This plasmid confers chloramphenicol resistance ($CM^R$), to cells and has lost the function of its $Tet^R$ gene ($Tet^S$), and produces K99. The plasmid thus created contains the K99 gene, but belongs to a different incompatibility group from that of the plasmid containing the K88 gene.

Transformation of *E. coli* K12 with these two plasmids resulted in cells which produced both K88 and K99, although instability was noted after a time. Such transformants may be utilized as described above in vaccination procedures.

EXAMPLE IV

This example, as mentioned above, relates to the utilization of a single plasmid containing both the gene for K88 and the gene for K99. The composite plasmid, designated pWD600, was 22.2 Kb in size and conferred chloramphenicol resistance ($CM^R$) and both K88 and K99 expression to the host cell. It was created by inserting the HindIII fragment including the K88 gene from pPS002 (12.1 Kb $Amp^R$, K88+) being inserted into plasmid pCTS3002 (10.65 Kb, $CM^R$, K99+). HindIII treatment of plasmid pCTS3002 was followed by alkaline phosphate treatment to prevent the plasmid from recircularizing on itself in the presence of T4 DNA ligase. The composite plasmid produced both antigens as assessed by agglutination tests, but the level of antigen production was lower than with each gene in a separate bacterium. However, the plasmid was stable and production continued.

These strains containing this composite plasmid may be utilized as described above in vaccination procedures.

EXAMPLE V

The LT gene was cloned from the plasmid p307 as described by So, M., Dallas, W. S., and Falkow, S., *Infect. Immun.* 21:405–411 (1978). A further series of steps produces the plasmid EWD299 as described in Dallas, W. S., Gill, D. M., and Falkow, S., *J. Bacteriol.* 139:850–858 (1979). The cistron that encodes for the B subunit of LT was then cloned individually into the expression vector pJJS500 by cleaving EWD299 with EcoRI and ligating this DNA to EcoRI cleaved pJJS500. A plasmid was identified which specified LT-B production but no LT-A production and was designated EWD1000. The LT-B cistron is being transcribed from the UV5 lac promoter in this plasmid.

Assays indicate 10–20% greater production of LT-B in the non-pathogenic strain compared to the pathogenic wild type strain.

It should be noted at this point that pJJS500 also is known to contain a gene for the surface antigen of Hepatitis B. This surface antigen, however, is not expressed and therefore will not be present in a final product. However, it may be desired to totally eliminate the gene for the Hepatitis B surface antigen. To do this, the plasmid pJJS500 is cut by the restriction enzyme HindIII and BamH-I to remove all of the gene for L-TB as well as the gene for the UV5 lac promoter. This fragment is then inserted into the plasmid pPM31 by inserting at the HindIII-BamH-I gap created after appropriate removal of this fragment from the pPM31. The resulting plasmid is $Tet^S$ (because part of the gene for tetracycline resistance is removed with the HindIII-BamH-I fragment). The plasmid is also absent for the gene for the Hepatitis B antigen.

EXAMPLE VI

LT-B and K88 have been produced in the same host from the two different plasmids pPS002 and EWD1000, as created in Examples I and V above. These composite plasmids are of different compatibility groups and so are stable in the same host. The antigen production is similar to previously discussed results.

In all of the foregoing examples, it is desirable that genes for antibiotic resistance be eliminated from the plasmids utilized. It is preferable to not have resistant genes in vaccines and these may be replaced by genetic elements, conferring the ability on the microorganisms constitutive expression of enzymes necessary for lactose utilization, allowing easy identification of bacteria with the recombinant plasmids.

It may be seen, therefore, that the invention provides improved vaccines and an improved vaccination procedure in which live or attenuated or killed non-pathogenic microorganisms are used. Thus, other toxins produced by the microorganisms, or other disease-carrying factors, are not present in the vaccine. A vaccine which is live and which contains a suitable adhesin factor along with the non-toxic antigenic determinant for a gastroenteric toxin could permanently colonize in the gastrointestinal tract, conferring long lasting immunity.

Various modifications of the invention in addition to those shown and described herein will become apparent to those skilled in the art from the foregoing description. Such modifications are intended to fall within the scope of the appended claims. For example, adhesins which may be used according to the present invention include 987P.

What is claimed is:

1. A vaccine for the prevention of gastroenteric disease caused in mammalian species by a pathogenic *Escherichia coli*, said vaccine comprising recombinant cells of a nonpathogenic *E. coli*, wherein said recombinant *E. coli* express genes encoding:
   (i) a pathogenic *E. coli* adhesin and
   (ii) a toxoid of a pathogenic *E. coli* toxin causative of the disease.

2. A vaccine according to claim 1 wherein the adhesin is selected from K88, K99, and 987P.

3. A vaccine according to claim 1 wherein the toxoid is LT-B.

4. A vaccine according to claim 1 wherein the adhesin is K88 and the toxoid is LT-B.

5. A recombinant *Escherichia coli* suitable for use in a vaccine for prevention of gastroenteric disease caused in a mammalian species by a pathogenic *Escherichia coli*, wherein said transformed *E. coli* express genes encoding:
   (i) a pathogenic *E. coli* adhesin and
   (ii) a toxoid of a pathogenic *E. coli* causative of the disease.

6. The cells of claim 5, wherein the adhesin is selected from K88, K99, and 987P.

7. The cells of claim 5, wherein the toxoid is LT-B.

8. The cells of claim 5, wherein the adhesin is K88 and the toxoid is LT-B.

9. A method for making a vaccine for the prevention of gastroenteric disease in a mammalian species by a pathogenic *Escherichia coli* comprising inserting into non-pathogenic *E. coli* genes encoding
   (i) a pathogenic *E. coli* adhesin and
   (ii) a toxoid of a pathogenic *E. coli* causative of the disease
   thereby obtaining a recombinant *E. coli*;
   wherein said recombinant *E. coli* express said genes.

10. The method of claim 9, wherein the adhesin is selected from K88, K99, and 987P.

11. The method of claim 9, wherein the toxoid is LT-B.

12. The method of claim 9, wherein the adhesin is K88 and the toxoid is LT-B.

13. A method of vaccinating a member of a mammalian species for prevention of gastroenteric disease caused by a pathogenic *Escherichia coli* comprising administering to said member in the form of a vaccine the cells of claim 1.

14. A method of vaccinating a member of a mammalian species for prevention of gastroenteric disease caused by a pathogenic *Escherichia coli* comprising administering to said member in the form of a vaccine the cells of claim 6.

15. A method of vaccinating a member of a mammalian species for prevention of gastroenteric disease caused by a pathogenic *Escherichia coli* comprising administering to said member in the form of a vaccine the cells of claim 7.

16. A method of vaccinating a member of a mammalian species for prevention of gastroenteric disease caused by a pathogenic *Escherichia coli* comprising administering to said member in the form of a vaccine the cells of claim 8.

17. A method of vaccinating a member of a mammalian species for prevention of cholera comprising administering to said member in the form of a vaccine the cells of claim 1, wherein the toxoid is LT-B.

* * * * *